United States Patent [19]

Hicklin et al.

[11] Patent Number: 5,501,948
[45] Date of Patent: Mar. 26, 1996

[54] STABILIZED HEPATITIS B E ANTIGEN SUITABLE FOR IMMUNOASSAYS

[75] Inventors: Daniel J. Hicklin, Jersey City, N.J.; Charles T. Tackney, Brooklyn, N.Y.; Harlan W. Waksal, Upper Montclair, N.J.

[73] Assignee: ImClone Systems Incorporated, New York, N.Y.

[21] Appl. No.: 254,475

[22] Filed: Jun. 6, 1994

Related U.S. Application Data

[63] Continuation of Ser. No. 35,560, Mar. 22, 1993, abandoned, which is a continuation of Ser. No. 808,842, Dec. 16, 1991, abandoned, which is a continuation-in-part of Ser. No. 476,747, Feb. 7, 1990, abandoned, which is a continuation-in-part of Ser. No. 307,900, Feb. 6, 1989, abandoned.

[51] Int. Cl.$^6$ ..................................................... C12Q 1/70
[52] U.S. Cl. ............................. 435/5; 435/69.3; 436/518; 436/820
[58] Field of Search ........................... 435/5, 172.1, 7.93, 435/7.94, 69.3; 935/81; 436/518, 820

[56] References Cited

U.S. PATENT DOCUMENTS 4,563,423  1/1986  Murray et al. ........................ 435/69.3
4,758,507  7/1988  Murray et al. ............................ 435/5

OTHER PUBLICATIONS

Slusarczyk et al., Association of hepatitis B e antigen (HBeAg) with the core of the hepatitis B virus (HBcAg). Liver 5:48–53 (1985).

MacKay et al., The conversion of hepatitis B core antigen synthesized in *E. coli* into e antigen. J. Med. Virol. 8:237–243 (1981).

Yoshizawa et al., Demonstration of hepatitis B e antigen in hepatitis B core particles obtained from the nucleus of hepatocytes infected with hepatitis B virus. J. Gen. Virol. 42:513–519 (1979).

Takahashi et al., Immunochemical structure of hepatitis B e antigen in the serum. J. Immunol. 130:2903–2907 (1983).

Ma et al., Effect of pre-core and portion of core sequence on the expression of HBcAg in *E. coli*. Laboratory of Molecular Genetics, Institute of Basic Medical Sciences, Beijing, P.R. China.

Spiezia et al., Re-examination and further characterization of a monoclonal antibody to hepatitis B e Antigen (anti--HBe). J. Virol. Methods 13:351–362 (1986).

Oellerich, "Enzyme–Immunoassay: A Review", *J. Clin. Chem. Clin. Biochem.*, vol. 22, No. 12, pp. 895–904, 1984.

*Primary Examiner*—Toni R. Scheiner
*Assistant Examiner*—Donna Wortman
*Attorney, Agent, or Firm*—Campbell and Flores

[57] ABSTRACT

Methods and materials for producing hepatitis virus HBe antigenic proteins useful in immunoassays without the necessity of maintaining these proteins in denaturing environments are disclosed. Assay methods and materials utilizing these HBe proteins are also provided.

12 Claims, No Drawings

STABILIZED HEPATITIS B E ANTIGEN SUITABLE FOR IMMUNOASSAYS

This application is a continuation-in-part continuation of application U.S. Ser. No. 08/035,560, filed Mar. 22, 1993, now abandoned, which is a continuation of U.S. Ser. No. 07/808,842, filed Dec. 16, 1991, now abandoned, which is a continuation-in-part of U.S. Ser. No. 07/476,747, filed Feb. 7, 1990, now abandoned, which is a continuation-in-part of U.S. Ser. No. 07/307,900, filed Feb. 6, 1989, now abandoned, the entire specification of each of which is incorporated herein by reference.

TECHNICAL FIELD

The invention relates to hepatitis antigens for use in immunoassays. In particular, it concerns stabilized hepatitis B antigens which can be readily used in standard assays for the presence of hepatitis B anti-e antibodies.

BACKGROUND ART

The course of hepatitis B virus (HBV) infection in humans can be monitored by following the appearance and disappearance of certain components in plasma or serum of infected subjects. There appear to be three major HBV antigenic proteins: HBs, the envelope protein or surface antigen; HBc, or core antigen; and HBe antigen, which appears to be a processed product of the core. Antibodies are formed to all three of these antigens. The core antigen, HBc, does not appear as such in the plasma of infected subjects, however, its processed product HBe, along with HBs, are found in the plasma within several months after infection, and then effectively disappear. Antibodies reactive with core (anti-HBc) begin to appear about two months after infection and concentrations in plasma of antibodies reactive with HBe antigen (anti-HBe) peak around 4 to 5 months after infection. Anti-HBs antibody titers rise more or less concomitantly with the diminution of titers of anti-HBe. Thus, by assessing the levels of all five plasma-borne components, HBs, HBe, anti-HBs, anti-HBe, and anti-HBc, the status of the infection can be assessed. Commercially available assay kits provide tests for all of these markers.

Although HBc antigenic activity is not detected in plasma of infected individuals, particles containing the core antigen can be isolated. It has been known for over ten years that HBe antigen is released from these core particles by treatment with pronase, with pronase and 2-mercaptoethanol, with sodium dodecyl sulfate and 2-mercaptoethanol, or through disruption by sonication and treatment with chaotropic agents. Therefore, it is assumed that HBe is some sort of processed product of HBc, and that when HBc is produced in mammalian systems, its antigenic characteristics are converted to those of HBe. However, it has appeared that in order to maintain the anti-HBe characteristics of the processed antigen, denaturing conditions must be maintained. If the "processed" protein is put back into isotonic solution, it reassumes the antigenic properties of HBc.

As proteolytic cleavage appears to be involved in converting HBc to HBe, it is also known that the HBe antigen (or mixture of antigens) is a shorter molecular weight form of HBc. The native coding sequence and the deduced amino acid sequence for HBc have been known for some time (see, for example, U.S. Pat. No. 4,710,463 to Biogen).

U.S. Pat. Nos. 4,758,507 and 4,563,423, both assigned to Biogen, describe the recombinant production of putative HBe. Briefly, the methods involve recombinant production of HBc in bacteria and subsequent treatment with reagents to convert the HBc product to HBe. In illustrative embodiments, HBc of about 1% purity is treated either with 0.1% pronase or with 0.1% pronase and 0.1% mercaptoethanol. Alteratively, 1% SDS and 10 mM 2-mercaptoethanol are used. It is further suggested that the HBe recombinant protein could be prepared by chewing back the HBc gene to an appropriate but unspecified location to generate HBe peptide. However, the HBe produced by these methods, even the putatively shortened form, require the presence of denaturing agents to maintain HBe antigenicity.

European application No. 87117370.4 (Publication No. 0,272,483) assigned to Abbott Laboratories describes recombinant production of HBe from a C-terminal deleted HBc gene and maintenance of HBe antigenic characteristics by treatment with and storage in guanidine. Again, removal of the chaotropic agent results in resumption of HBc rather than HBe antigenic characteristics.

There thus exists a need for a method of maintaining the antigenic characteristics of HBe without the use of denaturing or chaotropic agents. The present invention satisfies this need and provides related advantages as well.

SUMMARY OF THE INVENTION

The invention provides stable forms of Hepatitis B antigen useful in immunoassays for the titration of anti-HBe in the blood of HBV-infected subjects. It has now been found that HBe antigen suitable for immunoassays for detection of anti-HBe can be maintained by immobilizing the protein on a solid substrate. Such immobilization results in maintenance of the HBe antigen characteristics.

In one aspect, therefore, the invention is directed to an HBe antigen in immobilized form, captured on a solid support coated with anti-HBe. In other aspects, the invention is directed to methods to conduct immunoassays using the HBe antigens of the invention, and to materials, such as derivatized solid supports, useful in these assays.

DETAILED DESCRIPTION OF THE INVENTION

An antigen is referred to in this specification as HBeAg or HBe antigen if it is unstable and is recognized with high specificity by antibodies to human e antigen, but not by antibodies to human core antigen. As used herein, specificity may be measured by following the procedure of Example IC. An optical density ratio of positive controls to negative controls as determined in accordance with the procedure of Example IC indicates high specificity if the ratio is at least 5, preferably at least 10, and more preferably at least 15. For practical reasons, the ratio will not normally exceed 100.

The structure of human e antigen is uncertain. It is possible that what is commonly referred to as "human e antigen" is a mixture of antigens.

HBeAg or HBe, as used herein, cover all unstable analogs of human e antigen that are recognized with high specificity by antibodies to human e antigen. Unstable analogs are proteins that otherwise satisfy the present definition of HBeAg but that revert to HBcAg too rapidly or with too high a probability to satisfactorily provide sufficient e antigenicity to be suitable as a reagent in an assay for anti human e antigen. This definition of HBeAg applies, for example, to the e antigens disclosed in U.S. Pat. Nos. 4,758,507 and 4,563,423 as well as to those disclosed in European Patent application 272,483.

This invention provides stabilized HBe antigen suitable for use in immunoassays to detect the presence of anti-HBe immunoglobulins. Such stabilized HBe retains its HBe antigenicity during storage, without providing extraneous and potentially deleterious stabilizing factors such as reducing or chaotropic agents. HBe is stabilized by being immobilized, by being bound to anti-HBe antibodies attached to a solid substrate.

Purified HBeAg is commercially available, for example, from Alpha Therapeutics, San Antonio, Texas. Alternatively, recombinant HBeAg can be produced by methods well known in the art. See for example, U.S. Pat. Nos. 4,758,507 and 4,563,423, and European patent application 272,483, which are incorporated herein by reference.

HBe can be coated directly onto a solid substrate. However, over time, such coated HBeAg exhibits decrease in E antigenicity, and a decrease in core immunoreactivity. In a solid phase configuration where HBe is captured onto a solid substrate coated with anti-HBe antibodies, the retention of E antigenicity is improved. Preferably, the solid phase configuration is produced as follows: HBe antigen in a chaotropic solution, such as guanidine-dithiothreitol, is diluted, for example with a high protein containing diluent, and incubated with a solid substrate, such as microtiter wells, previously coated with anti-HBeAg antibody. The high protein diluent may, for example, be plasma, serum, BSA, or gelatin. The HBeAg guanidine:DTT ratio is adjusted so that a high anti-HBeAg assay reading is achieved (0.85–1.a.20 O.D.) with negligible anti-core reactivity (<0.150 O.D.). The concentration of guanidine and DTT must be adjusted so as not to interfere in the antibody-antigen reaction while still maintaining the molecule in a non-conformational state. Once captured by the anti-HBeAg antibodies on the plate, the chaotropic agent can be removed and the wells dried for future use. This solid phase configuration has improved stability under normal storage conditions, compared to that of solubilized HBe.

The solid phase captured HBeAg can be used in a one step assay to detect the presence of anti-HBeAg antibodies in a sample by competitive inhibition. A labeled antibody to HBe is used for competitive binding with antibodies in the sample to the immobilized HBeAg. The antibody may be labeled with a moiety that can be detected. The label may, for example, be a radioactive atom, a colometric group or an enzyme. The antibody may be monoclonal or polyclonal. The preferred antibody is polyclonal anti-HBe conjugated to horseradish peroxidase. Such an assay provides a specific, sensitive assay to detect anti-HBeAg antibodies. Additionally, the assay components are relatively stable at room temperature.

As used herein "Hepatitis Be Antigen" or "HBe Antigen" or "HBeAg" refers to a polypeptide having the antigenicity profile of HBe. The stabilized HBe of the present invention refers to a polypeptide which continues to express HBe antigenicity in solution, without the necessity of providing stabilizing factors, such as guanidine. It is understood, however, that limited modifications may be made without destroying the HBe antigenicity.

As used herein, "HBe antigenicity" refers to the reactivity of HBeAg with antibodies which specifically recognize and bind to HBe and the lack of cross reactivity with antibodies which specifically recognize and bind to HBc antigens. Kits to measure HBe antigenicity and HBc antigenicity are presently available from Abbott Laboratories. Antibodies which react with HBeAg are termed anti-HBe, anti-HBeAg antibodies, or anti-HBeAg Ig.

The following examples are intended to illustrate, but not limit, the invention.

EXAMPLE IA

Cloning the HBV Genome in *Escherichia coli*

Complete genomic HBV nucleic acid was isolated from the serum of an infected male patient who was positive for S antigen type ayw and e antigen by ELISA with specific serotype reagents and Auszyme and Hbe EIA kits, respectively (Abbott Laboratories, Deerfield, Ill.). Clarified serum was subjected to ultracentrifugation at 45,000 rpm for 3 hours at 10° C. to yield a virus pellet. The supernatant fluid was aspirated and the pellet resuspended in 500 µl at 50 mM Tris HCl pH 7.5, 50 mM NaCl. The virus preparation was layered onto a 20% sucrose solution in a SW41 rotor (Beckman Instruments, Brea, Calif.) and pelleted at 30,000 rpm for 4 hours at 4° C. The resulting virus pellet was resuspended in 50 mM Tris HCl pH 7.5, 10 mM $MgCl_2$, 5 mM 2-ME, 0.05% BSA, 10 mM NaCl, 0.5 mM EDTA.

Taking advantage of the endogenous virus polymerase, the gapped circular virus DNA was "filled in" by reaction with 10 mM each of dATP, dTTP, dGTP, dCTP at 37° C. for 2 hours. This in situ restoration of the circular structure makes subsequent cloning of the 3.2 kbp genome practical. Repaired particles were lysed in a buffer consisting of 10 mM Tris HCl, pH 7.5, 50 mM NaCl, 0.05% SDS, 20 µg/ml proteinase K. This solution was incubated at 37° C. for 1 hour, followed by phenol-chloroform and ether extractions to remove protein. Viral DNA was brought to 0.3M Na+ and precipitated with ethanol at 0° C. overnight. The resultant pellet of nucleic acid was dissolved in 10 mM Tris HCl pH 7.5, 1 mM EDTA, and the extinction at 260 nm measured. A suitable aliquot was removed and digested with the restriction endonuclease EcoRI. HBV nucleic acids contain a single, unique cleavage site for this enzyme, and yield a linear molecule upon digestion of 3.2 kbp. Linear HBV DNA with EcoRI termini was added to similarly digested vector pBR322 DNA in a ratio of 1 µg HBV/0.5 g PBR322 plasmid. Following ethanol precipitation and drying, the pellet was ligated with DNA ligase enzyme, and an aliquot added to competent HB101 bacterial cells (ATCC Rockville, Md.) (Boyer, H., and Roulland-Dussiox, D., *J. Molec. Biol.* 41:459 (1969)). Colonies that had taken up plasmids were scored and isolated on agar plates containing 50 mg/ml ampicillin.

Recombinant plasmids were identified by restriction enzyme analysis on agarose gels and by hybridization to radio-labelled probe. The probe can be $^{32}$p-marked virus nucleic acid or specific oligonucleotide probes labelled at the 5' end with kinase enzyme. Hybridization is best accomplished by colony lift techniques employing nitrocellulose membranes, essentially as in Grunstein, M. and Hogness, D., *Proc. Natl. Acad. Sci.* U.S.A., 72:3961 (1975) which is incorporated herein by reference. Individual colonies that contained a 3.2 kbp EcoRI insert into the 4.4 Kbp PBR322 plasmid were isolated and expanded for large-scale growth to isolate recombinant plasmids by CSCI gradient centrifugation. Methods well known in the art were employed to isolate plasmid recombinants free of bacterial DNA contaminants (See for example Maniatis, et al., (1982) *Molecular Cloning: A Laboratory Manual* (Cold Spring Harbor Laboratory) Cold Spring Harbor, N.Y.) which is incorporated herein by reference).

EXAMPLE IB

Production of Recombinant HBeAg

The plasmid recombinant isolated in Example IA was digested with the nuclease Nla III, (New England Biolabs, Beverly, Mass.) resulting in an 0.9 kbp restriction fragment. This fragment spans coordinates 1902–2849 of the HBV genome. The restriction fragment was cloned into plasmid pUC19 at the SphI cleavage site, resulting in recombinant plasmids with rightward (plus) and leftward (minus) directions of the inserted fragment. The correct (plus) orientation restriction fragment was chosen by routine restriction enzyme analysis. This plasmid was digested with HindIII and PstI. The resulting small HindIII/PstI fragment was cloned into pKK233-2 (Pharmacia Fine Chemicals, Piscataway, N.J.) at the HindIII and PstI sites, bringing the desired gene into a proper reading frame with the trc promoter (fused tryptophan and lactose promoters). This plasmid, which also contains the gene for ampicillin resistance, is designated pC7.

When expressed in *E. coli* strain HB101 (American Type Culture Collection, Rockville, Md.), pC7 produces a 20 kD monomer of HBVc, designated C7, which is capable of spontaneous self-assembly to a particle size in excess of $2 \times 10^6$ daltons. The assembled particles of C7 are highly immunoreactive with antibodies to C7. The amino and carboxy termini of C7 are identical to those of native HBcAg.

Using techniques of in vitro site directed mutagenesis (Kunkel, T. A., et al. *Methods in Enzymology*, 154, 367–382 (1987)), a TAA termination sequence was inserted at position 2349. The insertion was achieved using an oligonucleotide synthesized via solid phase chemistry, using a Cyclone DNA Synthesizer (Biosearch, Inc.). The oligonucleotide had the following sequence (TAA at position 2349 is underlined):

*GGACCTGCCTCGTCGGGTACCCTAAACAACAGTAGTCTCC*

This sequence is homologous to the sequence of pC7 flanking the position at which the mutation was desired. The desired TAA sequence was incorporated into the recombinant pC7, designated pCTM-18, as described by Kunkel et al. The insertion of TAA at position 2349 results in premature protein synthesis interruption and shortens the resulting molecule by 5 Kd, the natural terminator of HBcAg being at position 2450. This protein product, designated CTM-18, has the same carboxy terminus as HBe purified from human sera following processing of HBcAg in mammalian cells.

EXAMPLE IC

Specificity of e Antigen

Six wells are coated with 10 g each of polyclonal antibodies to human e antigen obtained from plasma. CTM-18 is denatured with guanidine in accordance with Example 5 of European patent application EP 272,483 (Abbott). Following denaturation, the solution containing the e antigen is immediately diluted to less than 0.1M guanidine in an appropriate medium in order to prevent the guanidine from precluding the binding of CTM-18 to the antibody. 150 ng of denatured CTM-18 in 100 µl of the medium are added to three of the wells and incubated at 37° C. for 12–18 hours. An appropriate medium is plasma; serum, or 0.01 molar carbonate buffer (pH 9.5). These wells contain the positive controls. No e antigen was added to the remainder of the wells in the negative controls. Wells are aspirated and washed 5× with 300 µl per well of PBS TWEEN™, a detergent. Each well is incubated for one hour at 37° C. with approximately 10 µg/100 µl of polyclonal antibodies to human e antigen conjugated to horseradish peroxidase in a solution of 50% calf serum, 49% PBS, 1% horse serum, 0.05% detergent (TWEEN 20™) and 1 mM potassium ferricyanide. The plates are washed, and the optical density at 450 nM is measured.

EXAMPLE II

Coating of Substrate with Anti-HBeAg

High titer human anti-HBe serum was obtained from the New York Blood Center. The serum was purified as follows. The serum was precipitated with 50% ammonium sulfate at 4° C. for 4 hours. The precipitated IgG was pelleted by centrifugation, resuspended in phosphate buffered saline (PBS), pH 7.25 and dialyzed against phosphate-buffered saline, pH 7.25. The dialyzed IgG was then applied to a Baker Bond ABx HPLC column. Fractions determined to be IgG positive by anti-human IgG ELISA were pooled and concentrated by ultrafiltration on YM-30 membrane (Amicon, Danvers, Mass.). The purified serum was diluted in 25 mM Tris-HCl, pH 8.0 to a concentration of 15 µg/200 µL.

200 ML of diluted serum was placed in each well of (Dynatech Labs, Boston, Mass.) Immulon II 96 well polystyrene microtiter strip wells and allowed to incubate overnight at room temperature. The solution was pipetted off and 200 µL of 5% BSA in PBS allowed to overcoat for 30 minutes at 37° C. The wells were washed five times with 300 µL PBS. The anti-HBeAg coated wells can either be used immediately or stored for future use.

EXAMPLE III

Capture of HBeAg

Purified rHBeAg, prepared by the method of Example I, was reconstituted in 8M guanidine, 75 mM dithiothreitol (DTT; Sigma Chemical Co., St. Louis, Mo.) (100 µL/16 µg antigen). The solution was vortexed and allowed to incubate for three minutes. Immediately after incubation, the solution was diluted to a final concentration of 150 mM guanidine, 1.4 mM DTT in a diluent containing 25% normal human serum, 10% BSA in phosphate buffered saline pH 7.2. 100 µL of diluted antigen was then added to microtiter wells coated the previous day with anti-HBeAg sera according to the method of Example II, and allowed to incubate at room temperature for 24 hours. After incubation, wells were aspirated without washing and dried at 37° C. for 30 minutes in a low humidity incubator. The strips were sealed in laminated foil pouches with desiccant material (Multiform Desiccants Corp., Buffalo, N.Y.).

The immobilized antigen was determined to exhibit HBe antigenicity, but not HBc antigenicity. The same results were obtained after storage for one month, indicating stable E antigenicity.

EXAMPLE IV

Assay for Anti-HBe

Microtiter strip wells prepared as in Example III were removed from the storage pouch and washed three times with PBS. The plates were inverted on a clean paper towel and patted dry to remove any accumulation of fluid around the wells.

Three wells were used as positive controls and to each was added 50 μL of plasma from patients known to be immunoreactive for antibodies to Hepatitis B e antigen. 50 μL of plasma from individuals known to be non-reactive for hepatitis was added to three other wells as negative controls. 50 μL of plasma suspected of containing anti-HBe were added to each test well. All samples were obtained from New York Blood Center.

HRP conjugated anti-HBeAg was prepared as follows:

High titer human serum having anti-HBeAg reactivity was obtained from the New York Blood Center. Saturated ammonium sulfate was added dropwise (3 mL/minute), with stirring, to an equal volume of serum, and the solution stirred for an additional 30 minutes after the final addition. The solution was centrifuged at 2000 RPM for 30 minutes at 4° C. and the supernatant decanted. The pellet was resuspended to the original volume in PBS, pH 7.2. As before, saturated ammonium sulfate was added and the solution was centrifuged. The pellet was resuspended in one half the original volume of PBS, pH 7.2, and dialyzed overnight at 4° C. against PBS, pH 7.2.

The solution was chromatographed in a Baker Bond ABx HPLC Column equilibrated with 20 mM $KH_2PO_4$, pH 6.7, and eluted with 20 mM $KH_2PO_4$ and 50 mM $(NH_4)SO_4$, pH 6.7. Fractions positive for Ig, as determined by their functional use in an anti-HBeAg assay, were pooled and concentrated using an Amicon ultrafiltration cell with a YM-30 membrane.

Horseradish peroxidase (HRP) was conjugated to the anti-HBe antibodies according to the method of Wilson and Nakane "Immunofluorescence and Related Techniques" (Knapp et al., eds.) Elsevier North Holland, Amsterdam (1978), with minor modifications. Briefly, 4 mg HRP (Type VI RZ=3.0, Sigma Chemical Co., St. Louis, Mo.) was dissolved in 1.0 mL of 2 mM acetate buffer, pH 4.4, 0.2 mL freshly prepared 0.2M $NaIO_4$ (Sigma Chemical Co.) was added to the HRP solution and stirred for 20 minutes at room temperature. Excess $NaIO_4$ was removed by gel filtration on a 1×20 cm Sephadex G-25 (Pharmacia Fine Chemicals, Piscataway, N.J.) column equilibrated with 2 mM acetate buffer pH 4.4. Oxy-HRP fractions were pooled and concentrated to the original volume.

The pH of the HRP solution was raised to 9.5 by the addition of 20 μL 0.2M sodium bicarbonate buffer, pH 9.5. 9 mG of purified IgG in 1 mL 0.02M sodium bicarbonate buffer, pH 9.5 and stirred for 2 hours at room temperature. 0.1 mL of freshly prepared sodium borohydride solution (4 mg/mL in $H_2O$) and left overnight.

The solution was applied to a Baker Bond ABx HPLC column equilibrated with 20 mM 4-morpholine ethane sulfonic acid (MES), pH 5.6, and eluted with 500 mM $(NH_4)_2SO_4$, pH 7.0. Fractions were screened for activity at $O.D._{280}$ and $O.D._{403}$ and those fractions having the highest ratio of $O.D._{403}/O.D._{280}$ were pooled. BSA (10 mg/mL) and glycerol were added (to final concentration of 40%). The conjugate was titered, divided into 1 ml aliquots, and stored at −20° C.

The following conjugate diluent was used: 40% Newborn Bovine Serum (heat-inactivated), 10% Normal Human Serum (heat-inactivated), 1% horse serum (heat-inactivated), 0.05% aggregated immunoglobulin (human), 0.07% TWEEN-20™; a detergent, 1 mM potassium ferricyanide, amphotericin B (2.5 mg/mL), gentamicin sulfate (50 mg/mL), in 0.05M Tris and 0.15M NaCl, pH 7.4.

150 μL conjugate was added to each control or test well. The wells were covered and the plate agitated briefly and incubated at 37° C. for 120 minutes. The cover seal was removed and the wells washed 5 times with 1.5 ml PBS containing 0.05% TWEEN 20™, a detergent (Sigma Chemical Co., St. Louis, Mo.). The plate was inverted on a clean paper towel and patted dry.

150 μL substrate solution containing freshly mixed tetramethylbenzidene and hydrogen peroxide solutions (Kirkegaard & Perry Labs, Gaithersburg, Md.) was added to each well and incubated in the dark at room temperature. 50 μL stop solution containing 4N sulfuric acid was added to each well and the plate agitated gently.

The plates were read in a Molecular Devices VMAX Reader at 450 nm.

EXAMPLE V

Stability of Solid Phase Captured HBeAg

An accelerated stability study was conducted on solid phase captured HBeAg (prepared by the method of Example IC) to determine the persistence of the E antigenicity of the antigen. Strip wells were maintained at 37° C. in a low humidity chamber 21 days. E antigenicity was measured by O.D. units at 450 nm using the assay described in Example IV. The results are presented in Table I.

TABLE I

| Day | Reactivity |
|---|---|
| 0 | 1.284 |
| 1 | 1.263 |
| 2 | 1.278 |
| 3 | 1.235 |
| 4 | 1.204 |
| 5 | 1.210 |
| 6 | 1.153 |
| 7 | 1.136 |
| 8 | 1.203 |
| 9 | 1.159 |
| 10 | 1.116 |
| 11 | 1.146 |
| 12 | 1.093 |
| 13 | 1.075 |
| 14 | 1.106 |
| 15 | 1.095 |
| 16 | 1.061 |
| 17 | 1.025 |
| 18 | 0.963 |
| 19 | 1.010 |
| 20 | 0.985 |
| 21 | 0.972 |

As indicated, reactivity of captured antigen decreased 11.6% after 1 week at 37° C., 14.0% after 2 weeks at 37° C. and 24.3% after 3 weeks at 37° C. From these results it is predicted that captured antigen will retain acceptable stability for over 9 months at 37° C.

EXAMPLE VI

Specificity and Sensitivity of Anti-HBeAg Immunoassay

Clinical specificity and sensitivity were demonstrated by assaying 123 known negative and positive patient samples and correlating to the Abbott HBe (rDNA) EIA Diagnostic Kit (Abbott Laboratories, Deerfield, Ill.). 94 samples tested positive (O.D. .0.5) and 29 samples tested negative (O.D., 0.5) using duplicate assays according to the method of Example IV. There was a 100% correlation with the Abbott EIA. The following formula is used for the cutoff (09.5)× positive control+(0.5)×negative control=cutoff. An assay is considered valid when the P—N ($PC_x$—$NC_x$) value is greater than −0.5. Summary of the data are shown in Table II.

TABLE II

|  | ABBOTT EIA | IMCLONE EIA |
|---|---|---|
| Pos. Mean | .064 | 0.089 |
| Neg. Mean | 1.430 | 1.023 |
| Range | .715–2.145 | .512–1.533 |
| P-N | −1.367 | −0.934 |
| Cutoff | .747 | 0.556 |

Although the invention has been described with reference to the presently-preferred embodiment, it should be understood that various modifications can be made without departing from the spirit of the invention. Accordingly, the invention is limited only by the following claims.

We claim:

1. A method of stabilizing the antigenicity of hepatitis Be antigen, HBeAg, over time, comprising the steps of:

a. adsorbing anti-HBeAg antibodies to a solid support to form a coated solid support;

b. diluting previously denatured HBeAg into a non-denaturing solution;

c. capturing the HBeAg on said anti-HBeAg antibody coated support to form a second coating;

d. insolubilizing said captured HBeAg; and e. storing the captured and insolubilized HBeAg at temperatures up to 37° C. in low humidity conditions.

2. The method of claim 1, wherein the stabilized HBeAg is stored in low humidity conditions for at least 7 days.

3. The method of claim 1, wherein the stabilized HBeAg is stored in low humidity conditions for at least 21 days.

4. The method of claim 1, wherein the stabilized HBeAg is stored in low humidity conditions for at least 9 months.

5. The method of claim 1, wherein the solid support is a microtiter well.

6. The method of claim 1, wherein the HBeAg is made by recombinant DNA means.

7. A method of assaying a biological sample for anti-HBe antibodies, comprising the steps of:

a. contacting the biological sample with HBeAg stabilized according to claim 1, for a time sufficient to permit binding of anti-HBe antibodies to the immobilized HBeAg; and b. detecting the anti-HBe antibodies bound to said stabilized HBeAg.

8. The method of claim 7, wherein said solid support is a microtiter well.

9. The method of claim 7, wherein said detecting step further comprises detecting the competitive inhibition of binding of anti-HBe antibodies from the sample by labelled anti-HBe.

10. The method of claim 9, wherein said labelled anti-HBe antibodies are anti-HBe antibodies conjugated to an enzyme or a component of an enzymatic reaction.

11. The method of claim 10, wherein said enzyme is horseradish peroxidase.

12. A kit for detecting anti-HBe antibodies comprising HBeAg which has been stabilized according to claim 1, contained in a sealed container, and labelled anti-HBe antibodies.

* * * * *